(12) United States Patent
Pretzlaff et al.

(10) Patent No.: US 8,941,020 B2
(45) Date of Patent: Jan. 27, 2015

(54) LEAD FEEDTHROUGH AND ELECTRICAL FUNCTIONAL UNIT

(75) Inventors: Bernd Pretzlaff, Mildstedt (DE); Hans-Juergen Kuehl, Lunden (DE)

(73) Assignee: Litronik Entwicklungs GmbH, Husum (DE)

( * ) Notice: Subject to any disclaimer, the term of this patent is extended or adjusted under 35 U.S.C. 154(b) by 233 days.

(21) Appl. No.: 13/420,580

(22) Filed: Mar. 14, 2012

(65) Prior Publication Data

US 2012/0261183 A1    Oct. 18, 2012

Related U.S. Application Data

(60) Provisional application No. 61/475,685, filed on Apr. 15, 2011.

(51) Int. Cl.
| | |
|---|---|
| *H02G 3/18* | (2006.01) |
| *H01G 11/78* | (2013.01) |
| *A61N 1/375* | (2006.01) |
| *H01G 9/008* | (2006.01) |
| *H01G 9/10* | (2006.01) |
| *H01G 11/74* | (2013.01) |
| *H01G 11/80* | (2013.01) |

(Continued)

(52) U.S. Cl.
CPC .............. *H01G 11/78* (2013.01); *A61N 1/3754* (2013.01); *H01G 9/008* (2013.01); *H01G 9/10* (2013.01); *H01G 11/74* (2013.01); *H01G 11/80* (2013.01); H01M 2/06 (2013.01); H01M 2/08 (2013.01); Y02E 60/13 (2013.01)
USPC .......................................... 174/650; 361/302

(58) Field of Classification Search
CPC ........................... A61N 1/3754; A61N 1/3752
USPC .......... 174/650, 667, 113 R, 152 G, 152 GM, 174/520, 50.5; 607/37, 86, 92, 36, 38, 238; 361/302, 307, 306.1, 320
See application file for complete search history.

(56) References Cited

U.S. PATENT DOCUMENTS

| | | | | |
|---|---|---|---|---|
| 3,757,789 A | * | 9/1973 | Shanker | ........................ 607/37 |
| 5,930,109 A | | 7/1999 | Fishler | |

(Continued)

FOREIGN PATENT DOCUMENTS

| | | |
|---|---|---|
| WO | 2005/001997 | 1/2005 |
| WO | 2009/015438 | 2/2009 |

OTHER PUBLICATIONS

European Search Report dated Jun. 3, 2013, 8 pages.

*Primary Examiner* — Yuriy Semenenko
*Assistant Examiner* — Pete Lee
(74) *Attorney, Agent, or Firm* — ARC IP Law, PC; Joseph J. Mayo

(57) ABSTRACT

A lead feedthrough of an electrical functional unit, in particular a capacitor or medical electronic implant, which comprises a hollow conductive flange and a contact piece disposed in the cavity thereof and which is electrically insulated and sealed with respect to the flange, wherein the flange can be connected to a lead of a first type, and the contact piece can be connected to a lead of a second type in the functional unit, wherein, in a circumferential section of the flange, a tangentially extending gap is provided, which is delimited on one side by a flange body and on the other side by a tab integrally formed on the body, or by a separate pressure piece, for the tangential insertion and affixation of the lead of the first type.

17 Claims, 5 Drawing Sheets

(51) Int. Cl.
*H01M 2/06* (2006.01)
*H01M 2/08* (2006.01)

(56) References Cited

U.S. PATENT DOCUMENTS

| | | | |
|---|---|---|---|
| 6,586,675 B1 * | 7/2003 | Bealka et al. | 174/50.56 |
| 6,850,405 B1 | 2/2005 | Mileham et al. | |
| 7,623,335 B2 * | 11/2009 | Stevenson et al. | 361/302 |
| 7,696,002 B1 * | 4/2010 | Ribble et al. | 438/106 |
| 7,930,032 B2 * | 4/2011 | Teske et al. | 607/36 |
| 7,988,507 B2 * | 8/2011 | Darley et al. | 607/115 |
| 8,346,362 B2 * | 1/2013 | Kinney et al. | 607/37 |
| 2002/0142216 A1 | 10/2002 | Skoumpris | |
| 2004/0260354 A1 | 12/2004 | Bomstad et al. | |
| 2010/0134955 A1 * | 6/2010 | O'Connor et al. | 361/508 |

* cited by examiner

LEAD FEEDTHROUGH AND ELECTRICAL FUNCTIONAL UNIT

This application claims the benefit of U.S. Provisional Patent Application 61/475,685, filed on 15 Apr. 2011, the specification of which is hereby incorporated herein by reference.

BACKGROUND OF THE INVENTION

1. Field of the Invention

Embodiments of the invention relate to a lead feedthrough of an electrical functional unit.

2. Description of the Related Art

Feedthroughs that enclose a connecting lead are particularly critical regions in electronic devices and electrical components that must fulfill special requirements on permanent seal integrity. The design thereof has therefore been the subject of particular attention for years with respect to devices such as implantable medical electronic devices (pacemakers, implantable cardioverters, cochlear implants, implantable neurostimulators, etc.). A technically established aspect thereof is the formation of the feedthrough of suitable ceramic, especially enclosed by a metallic flange of the housing.

A feedthrough is described in WO 2005/001997 A2 especially for electrochemical components such as batteries or electrolyte capacitors, in the case of which a guide element composed of a polymer is provided for accommodating the connecting lead.

Document WO 2009/015438 A1 describes a method and a device for forming a lead feedthrough of a hermetically sealed container, which are characterized in that means and steps are provided for injecting an electrically insulating material into a cavity of the feedthrough.

Document US 2010/0134955 A1 describes a lead feedthrough of a multianode capacitor which has the basic design described initially. Hermetic seal integrity is attained in that case via a glass-to-metal seal, and a film-like lead section of the capacitor is welded to the outer surface of the flange of the feedthrough by laser welding.

BRIEF SUMMARY OF THE INVENTION

The problem addressed by at least one embodiment of the invention is that of providing an improved lead feedthrough of the stated type, which is relatively lightweight for lead connectors in particular that are difficult to handle, and which can be manufactured in a highly reliable manner.

This problem is solved by a lead feedthrough having the features as claimed herein and, according to a relatively independent aspect of at least one embodiment of the invention, by a lead feedthrough having the features of injectable plastic. Advantageous developments of at least one embodiment of the invention are also described herein. In conjunction with at least one embodiment of the invention, an electrical functional unit comprising a feedthrough according to at least one embodiment of the invention, and a method for manufacturing same are also provided.

One aspect of at least one embodiment of the invention is to provide a gap in the circumferential section of the flange for the insertion and affixation of leads of the electrical functional unit to be connected there. According to another aspect, said gap extends tangentially and is delimited on one side by a flange body. According to another aspect of at least one embodiment of the invention, the gap is delimited on the other side either by a tab, which extends at a distance from the flange body and is integrally formed thereon, or by a separately manufactured pressure piece which is brought into the predetermined position relative to the flange body in the process of manufacturing the feedthrough, and is retained there during assembly.

According to a first embodiment of the invention, the gap for the tangential insertion and affixation of one or, in particular, several leads of the first type designed as sheet or film have a flat cuboid shape. In particular, the tab or the pressure piece is designed with a flat prismatic shape, in particular as a flat cube or a flat trapezoid. This design is meaningful in particular when the flange body is substantially prismatic in shape or at least has a planar circumferential surface provided for contacting the aforementioned lead or the lead of the first type.

In an alternative embodiment, the gap for the tangential insertion and affixation of one or, in particular, several leads of the first type designed as sheet or film have the shape of a flat annular segment. In particular the tab or the pressure piece comprises a hollow cylindrical section in this case. This structural design is meaningful for a flange body having a substantially cylindrical outer shape.

In another structural embodiment, the flange comprises an end face which extends past the remaining circumference thereof and the maximum radial extension of the tab or the pressure piece. This is advantageous in the case of certain housing designs of the electrical functional unit for achieving an exact positioning of the feedthrough, and can fulfill a mechanical safeguard function.

According to the relatively independent aspect of the invention described above, the cavity in the flange is filled with a plug of injectable plastic which tightly encloses the contact piece and rests against the inner wall of the flange, likewise in a tight manner. As a result, a high degree of seal integrity of the housing in the region of the feedthrough is ensured in a manner that is technologically extremely simple and productive. In embodiments of said aspect, in order to attain larger creepage distances and/or larger adhesion surfaces, the plastic plug extends past the axial extension of the flange and, in particular, the radial extension thereof is greater in the overhanging section than that of the flange.

According to another embodiment of the invention, in the electrical functional unit equipped with a feedthrough according to at least one embodiment of the invention, the lead or leads of the first type are welded with the flange in or on the gap.

In an embodiment of the functional unit as capacitor in particular, a large number of leads of the first type, which are designed as cathode lugs, is provided; said leads are placed one on top of the other in the gap and are welded there to one another and/or with the flange. Although a capacitor of that type makes possible a preferred application of the invention, the use thereof is not limited to capacitors, but rather is also possible with other electrical or electronic devices or components, including, in particular electromedical implants such as pacemakers and implantable defibrillators or cardioverters. It is understood that a person skilled in the art will determine the specific structural design of the proposed feedthrough which is appropriate for the specific lead configuration of the particular device.

According to one method aspect of at least one embodiment of the invention, the lead or leads of the first type are inserted into the gap and are cold-welded by pressing the tab or the contact piece onto the flange body. According to an alternative embodiment, the lead or leads of the first lead type are inserted into the gap, and the free ends thereof are connected by laser welding.

In an embodiment of both variants, when a separate pressure piece is used, it is held in the intended position relative to the flange body by vacuum during insertion of the lead or leads.

According to another method-related embodiment of at least one embodiment of the invention, the plastic plug in the cavity of the flange is created by injection molding, wherein the flange and the contact piece are placed in an injection mold in the intended positional relationship to one another. Basically, two alternatives thereto are also feasible, such as inserting a suitably compressible yet gas-tight, prefabricated plastic plug into the flange.

BRIEF DESCRIPTION OF THE DRAWINGS

Advantages and useful features of the invention will also become apparent from the description that follows of embodiments with reference to the figures. In the figures.

DETAILED DESCRIPTION OF THE INVENTION

Figure 1:
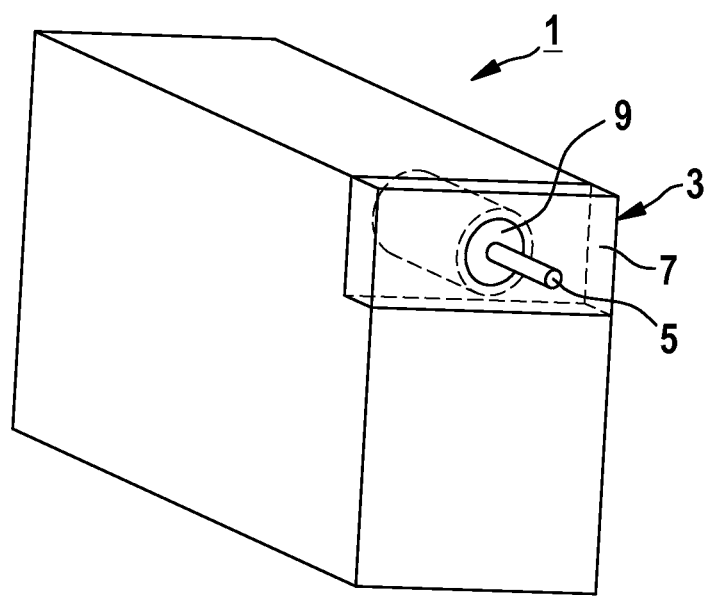
FIG. 1 shows a schematic perspective depiction of an electrical functional unit comprising a feedthrough.

FIG. 1 shows a schematic depiction of an electrical functional unit 1 comprising a feedthrough 3 inserted into a corner region, which comprises a centrally protruding contact piece 5, a flange 7 which encloses the contact piece and has a rectangular end face, and a plastic plug 9 which electrically insulates and seals the contact piece with respect to the flange. Functional unit 1 can be a capacitor or an implantable medical electronic device, for example.

Figure 2:
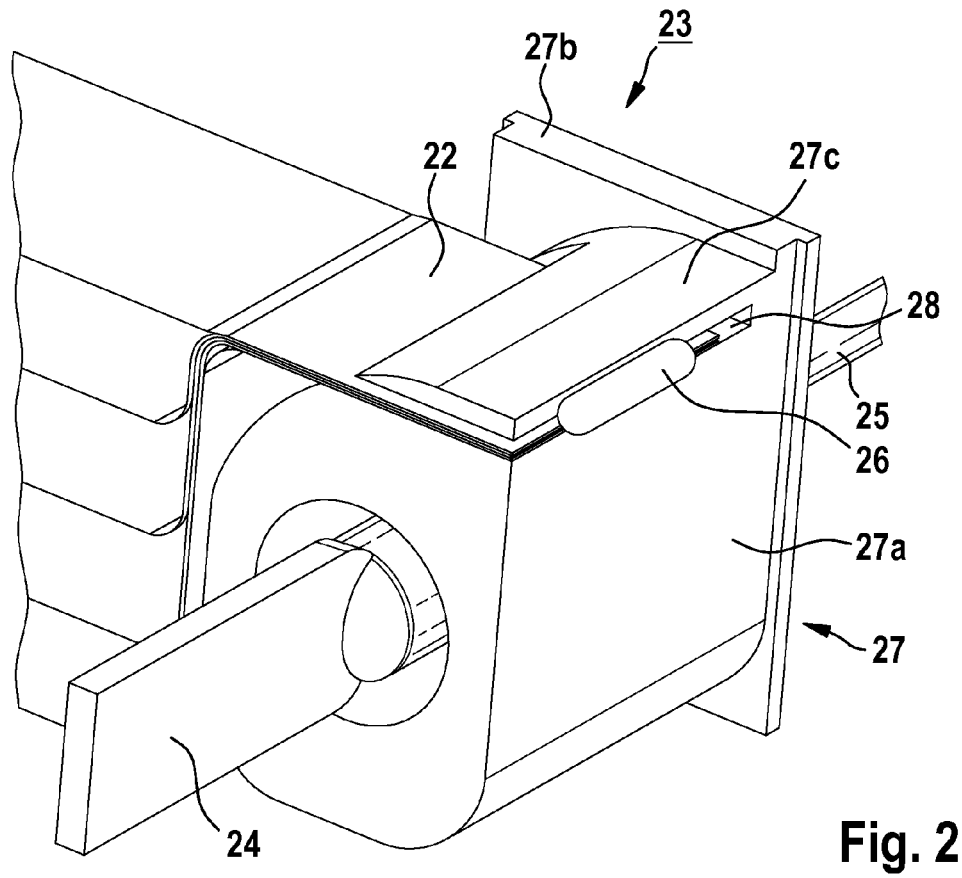
FIG. 2 shows a perspective depiction of a first embodiment of the feedthrough according to the invention.

FIG. 2 shows a feedthrough 23 of a capacitor (not shown in entirety), of which a plurality of cathode lugs 22 is shown. The reference characters used to label the parts of the feedthrough shown in FIG. 2 are based on the reference characters used in FIG. 1. Cathode lugs 22 are a lead of the first type (for example a lead with a flat annular segment), which is connected to flange 27 of the feedthrough, while a cuboid lead (a lead of the second type) 24 is connected to contact piece 25. Flange 27 comprises a body 27a, an end face 27b extending partially past the radial extension thereof, and a flat tab 27c extending parallel to the body starting from the end face. Tab 27c is integrally formed on end face 27b such that, between same and flange body 27a, a substantially cuboid gap 28 is determined, into which the ends of a large number of cathode lugs 22 can be inserted tangentially, and which are placed around a part of flange body 27a in the manner shown in the figure. Character 26 schematically represents a welding region of cathode lugs 22 with flange 27 formed by laser welding. In welding region 26, the cathode lugs (lead of the first type), which were inserted previously into gap 28 and affixed there temporarily, are securely connected to the flange as the outer part of feedthrough 23.

Figure 3:
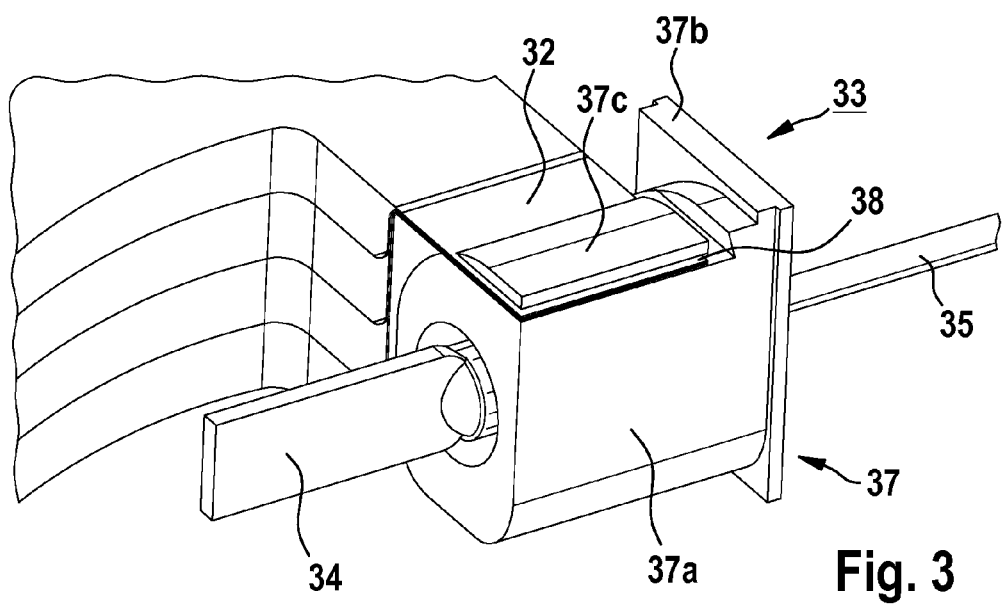
FIG. 3 shows a perspective depiction of a second embodiment of the feedthrough according to the invention.

FIG. 3 shows a modified embodiment of a feedthrough 33. The design thereof is largely similar to that of feedthrough 23 shown in FIG. 2, and so the reference characters used to label the individual parts are based on those used in FIG. 2, and the parts that are the same or similar are not explained again here. Cathode lugs 32 are a lead of the first type (for example a lead with a flat annular segment), which is connected to flange 37 of the feedthrough, while a cuboid lead (a lead of the second type) 34 is connected to contact piece 35. Flange 37 comprises a body 37a, an end face 37b extending partially past the radial extension thereof and a flat tab 37c extending parallel to the body starting from the end face. The main difference is that, instead of a tab integrally formed on the flange body, a separate pressure piece 37c is provided here, which determines gap 38 between same and flange body 37a for insertion of cathode lugs 32, and that the application of appropriately high pressure onto pressure piece 37c results in cold welding to cathode lugs 32 and flange body 37 (instead of the laser welding depicted in FIG. 2). In another embodiment, resistance welding is used to produce the connection.

FIGS. 4A to 4F show different variants of the geometric design of the flange and a plastic plug which fills the flange and encloses the contact piece disposed therein.

Figure 4C:
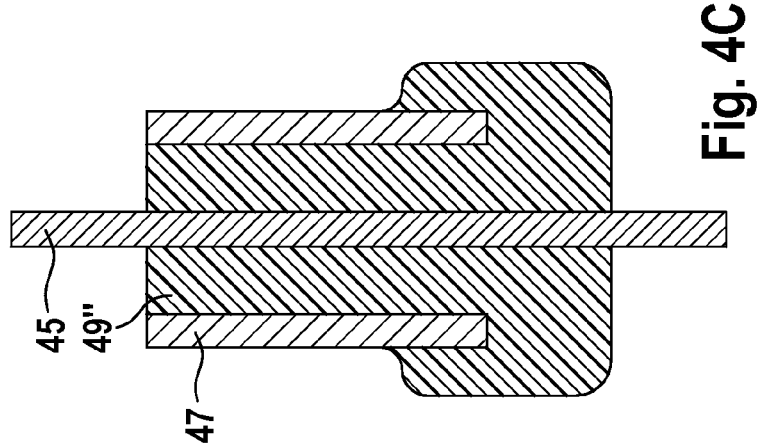
FIGS. 4A to 4F show schematic cross-sectional depictions and top views of flange-contact piece arrangements in embodiments of the feedthrough according to the invention.
Figure 4B:
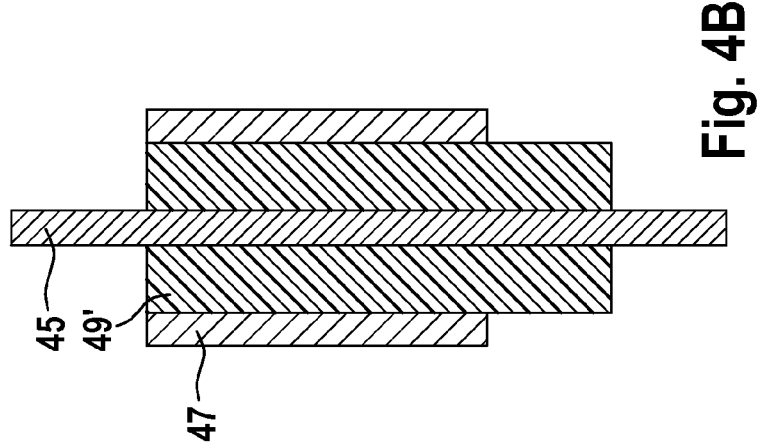
Figure 4A:
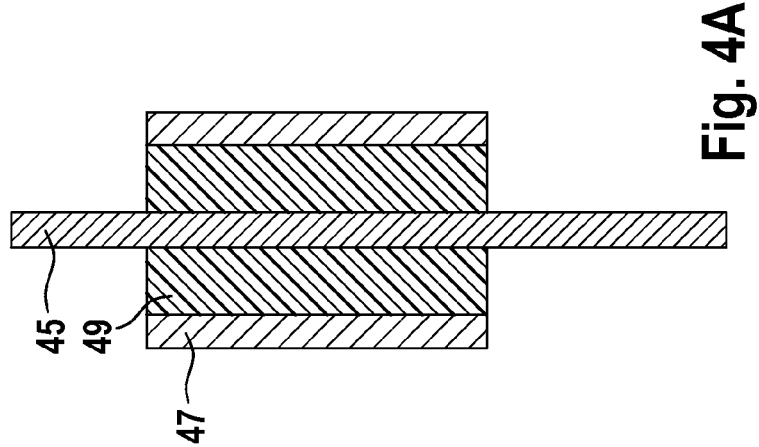

Although contact pieces 45 and flange 47 are identical in the embodiments shown in FIGS. 4A to 4C, three different plastic plugs 49, 49', and 49" are provided. Plastic plug 49' shown in FIG. 4B extends past the longitudinal extension of flange 47 while retaining the inner diameter of the flange as its own outer diameter in the overhanging part. In the embodiment shown in FIG. 4C, plastic plug 49" is also longer than flange 47, but has an enlarged diameter along approximately half of the longitudinal extension thereof, such that one end of the flange extends into the region of the enlarged diameter of the plastic plug and is embedded in same.

Figure 4D:
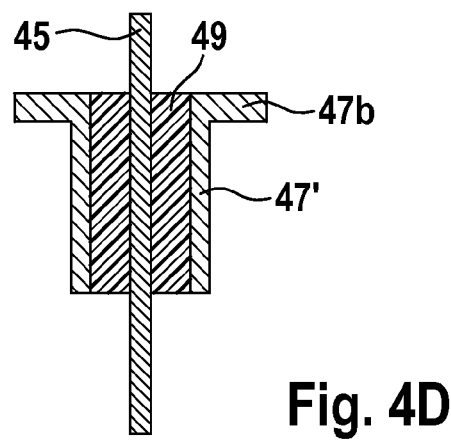
Figure 4E:
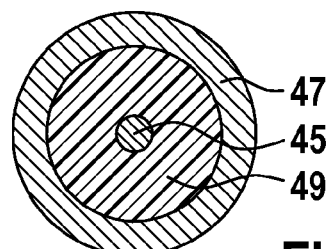
Figure 4F:
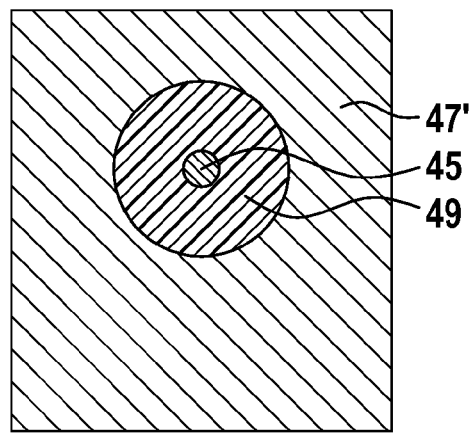

FIG. 4D shows a flange 47' comprising an integrally formed collar or end face 47b. While the end face of the design shown in FIG. 4A is shown in FIG. 4E, the top view of a flange provided with end face (the flange shown in FIG. 4E, for instance) can have the appearance of that shown in FIG. 4F.

Figure 5:
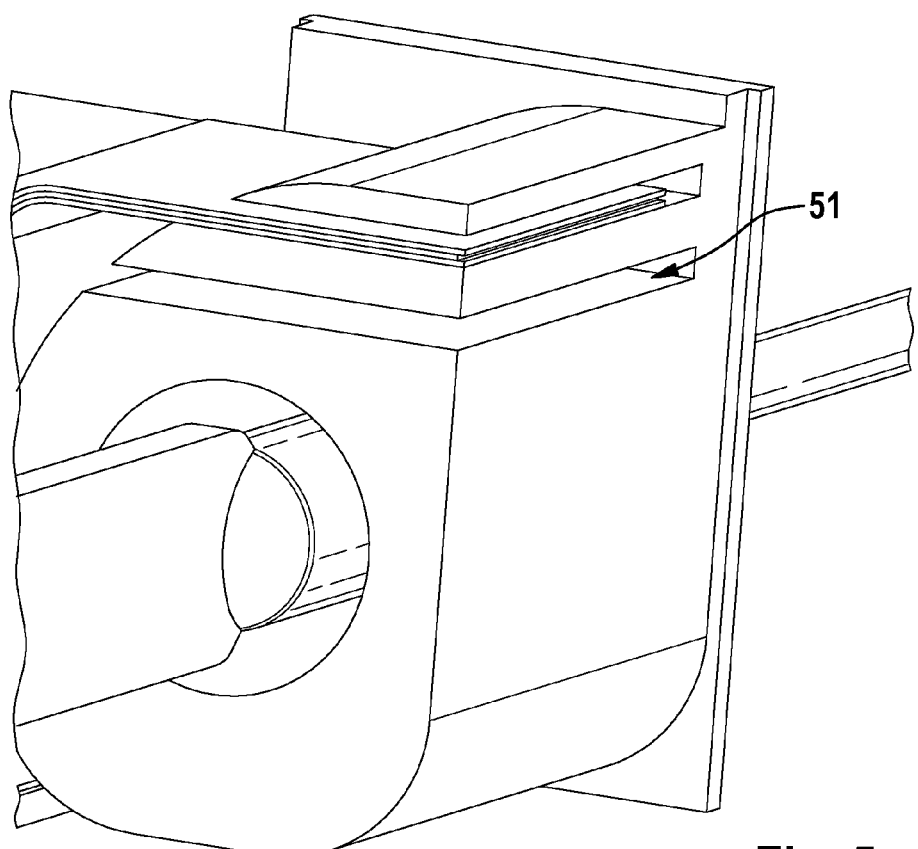
FIG. 5 shows a perspective depiction of another embodiment of the feedthrough according to the invention.

FIG. 5 shows another embodiment, in the case of which a second slot or gap 51 is provided. This slot or gap 51 is used to ensure that the seal is heated to a lesser extent by the welding of the terminals.

The embodiment of the invention is not limited to the above-described examples and emphasized aspects, but rather is possible in a large number of modifications that lie within the scope of a person skilled in the art. In particular, the seal can be in the form of a combination of glass and ceramic and plastic.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A lead feedthrough of an electrical functional unit that implements a capacitor or medical electronic implant, wherein said lead feedthrough comprises:
   a hollow conductive flange having a cavity, a flange end face, a flange flat tab and a flange body;
   a contact piece disposed in the cavity of said hollow conductive flange wherein the contact piece is electrically insulated and sealed with respect to the hollow conductive flange, and wherein said contact piece protrudes away from said hollow conductive flange;

wherein the hollow conductive flange is configured to connect to a lead of a first type, and wherein the contact piece is configured to be connected to a lead of a second type in the electrical functional unit;

wherein a circumferential section of the hollow conductive flange comprises a tangentially extending gap, which is delimited on one side by the flange body and on another side by a tab that extends at a distance from the flange body and is integrally formed on the flange body, or by a separate pressure piece, wherein said tangentially extending gap is configured to enable tangential insertion and affixation of the lead of the first type; and, wherein said tangentially extending gap comprises at least three open sides and enables said lead of the first type to be inserted and affixed orthogonal to said contact piece in at least one open side of said at least three open sides.

2. The lead feedthrough according to claim 1, wherein the tangentially extending gap configured to enable tangential insertion and affixation is configured to affix to one or several leads of the first type wherein said one or several leads of said first type are configured as sheet or film having a flat cuboid shape.

3. The lead feedthrough according to claim 2, wherein the tab or the separate pressure piece is configured in a flat prismatic shape, or shape of a flat cube or a flat trapezoid.

4. The lead feedthrough according to claim 1, wherein the tangentially extending gap configured to enable said tangential insertion and affixation is configured to affix one or several leads of the first type wherein said one or several leads of said first type are configured as sheet or film has the shape of a flat annular segment.

5. The lead feedthrough according to claim 4, wherein the tab or the separate pressure piece comprises a hollow-cylindrical section.

6. The lead feedthrough according to claim 1, wherein the hollow conductive flange comprises an end face which extends past a remaining circumference thereof and past a maximum radial extension of the tab or the separate pressure piece.

7. The lead feedthrough according to claim 1, further comprising a plug of injectable plastic and wherein the cavity of the flange comprises said plug of injectable plastic.

8. An electrical functional unit configured as a capacitor or medical electronic implant, and comprises a lead feedthrough, wherein said lead feedthrough comprises:

a hollow conductive flange having a cavity and a flange body;

a contact piece disposed in the cavity of said hollow conductive flange wherein the contact piece is electrically insulated and sealed with respect to the hollow conductive flange, and wherein said contact piece protrudes away from said hollow conductive flange;

wherein the hollow conductive flange is configured to connect to a lead or leads of a first type, and the contact piece is configured to be connected to a lead of a second type in the electrical functional unit;

wherein a circumferential section of the hollow conductive flange comprises a tangentially extending gap, which is delimited on one side by a flange body and on another side by a tab that extends at a distance from the flange body and is integrally formed on the flange body, or by a separate pressure piece, wherein said tangentially extending gap is configured to enable tangential insertion and affixation of the lead of the first type;

wherein the lead or leads of the first type is or are welded to the hollow conductive flange in or on the tangentially extending gap; and, wherein said tangentially extending gap comprises at least three open sides and enables said lead of the first type to be inserted and affixed orthogonal to said contact piece in at least one open side of said at least three open sides.

9. The electrical functional unit according to claim 8, wherein a large number of leads of the first type, which are configured as cathode lugs, are coupled one on top of the other in the tangentially extending gap and are welded to one another or are welded to the hollow conductive flange or are welded to one another and to the hollow conductive flange.

10. The electrical functional unit according to claim 8 wherein the lead or leads of the first type are configured to be inserted into the tangentially extending gap and are configured to be cold-welded through pressure between the tab or the contact piece and the body of the hollow conductive flange.

11. The electrical functional unit according to claim 8 wherein the lead or leads of the first type are configured to be inserted into the tangentially extending gap, and free ends thereof are configured to be connected by laser welding.

12. The electrical functional unit according to claim 11, wherein said separate pressure piece is configured to be held in an intended position relative to the body of the hollow conductive flange by vacuum during insertion of the lead or leads.

13. The electrical functional unit according to claim 10, further comprising a plastic plug configured to be injection molded in the cavity of the hollow conductive flange and wherein the hollow conductive flange and the contact piece are configured to be placed in an injection mold in an intended positional relationship to one another.

14. The lead feedthrough according to claim 1, wherein said flange flat tab comprises a flat planar bottom side and said flange body comprises a flat portion that parallels said flat planar bottom side of said flange flat tab that define said tangentially extending gap, such that said tangentially extending gap defines two planes.

15. The lead feedthrough according to claim 1, wherein said circumferential section of the hollow conductive flange further comprises a second tangentially extending gap configured to ensure that a seal is heated to a lesser extent.

16. The electrical functional unit according to claim 8, wherein said hollow conductive flange further comprises a flange end face and a flange flat tab, wherein said flange flat tab comprises a flat planar bottom side and said flange body comprises a flat portion that parallels said flat planar bottom side of said flange flat tab that define said tangentially extending gap, such that said tangentially extending gap defines two planes.

17. The electrical functional unit according to claim 8, wherein said circumferential section of the hollow conductive flange further comprises a second tangentially extending gap configured to ensure that a seal is heated to a lesser extent.

* * * * *